US008089047B2

(12) United States Patent
Boatner et al.

(10) Patent No.: US 8,089,047 B2

(45) Date of Patent: Jan. 3, 2012

(54) METAL-ORGANIC SCINTILLATOR CRYSTALS FOR X-RAY, GAMMA RAY, AND NEUTRON DETECTION

(75) Inventors: Lynn A Boatner, Oak Ridge, TN (US); James A. Kolopus, Clinton, TN (US); John S Neal, Knoxville, TN (US); Joanne Oxendine Ramey, Knoxville, TN (US); Dariusz J Wisniewski, Torun (PL)

(73) Assignee: UT-BaHelle, LLC, Oak Ridge, TN (US)

( * ) Notice: Subject to any disclaimer, the term of this patent is extended or adjusted under 35 U.S.C. 154(b) by 317 days.

(21) Appl. No.: 12/472,580

(22) Filed: May 27, 2009

(65) Prior Publication Data

US 2010/0301219 A1 Dec. 2, 2010

(51) Int. Cl.
*G01T 1/20* (2006.01)

(52) U.S. Cl. ............. 250/362; 250/301.33; 250/301.36; 250/301.4 R

(58) Field of Classification Search .................. 250/362; 252/301.33, 301.36, 301.4 R
See application file for complete search history.

(56) References Cited

OTHER PUBLICATIONS

L.A. Boatner, et al., "Single-Crystal CeCl3(CH3OH)4: A New Metal-Organic Cerium Chloride Methanol Adduct for Scintillator Applications," Applied Physics Letters, published online Dec. 16, 2008, pp. 244104-1 thru 1244104-3, vol. 93.

B.C. Chakoumakos, et al., "Cerium Chloride—Methanol Adduct Crystals, CeCl3(CH3OH)4: Preparation, Crystallography, and Scintillation Properties," Crystal Growth and Design, Published on Web Jun. 5, 2008, pp. 2070-2072, vol. 8, No. 7.

*Primary Examiner* — David Porta
*Assistant Examiner* — Christine Sung
(74) *Attorney, Agent, or Firm* — Joseph A. Marasco

(57) ABSTRACT

New metal-organic materials are useful as scintillators and have the chemical formula $LX_3(CH_3OH)_4$ where L is Y, Sc, or a lanthanide element, and X is a halogen element. An example of the scintillator materials is $CeCl_3(CH_3OH)_4$.

10 Claims, 6 Drawing Sheets

METAL-ORGANIC SCINTILLATOR CRYSTALS FOR X-RAY, GAMMA RAY, AND NEUTRON DETECTION

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

CROSS-REFERENCE TO RELATED APPLICATIONS

None

NAMES OF PARTIES TO A JOINT RESEARCH AGREEMENT

None

BACKGROUND OF THE INVENTION

Cerium trichloride is a well-known inorganic scintillator that represents one member of a family of inorganic, rare-earth scintillators, including the high-light-yield, high-energy-resolution member, $LaBr_3:Ce^{3+}$. These hygroscopic, inorganic, rare-earth halides are conventionally grown as single crystals from the melt by either the Bridgman or the Czochralski technique, protracted and expensive processes that are characterized by severe cracking of the material due to anisotropic thermal stresses and cleavage effects. Therefore, such materials are not generally considered to be preferable for applications requiring large crystal scintillators.

For a better understanding of the present invention, together with other and further objects, advantages and capabilities thereof, reference is made to the following disclosure and appended claims in connection with the above-described drawings.

DETAILED DESCRIPTION OF THE INVENTION

Figure 1:
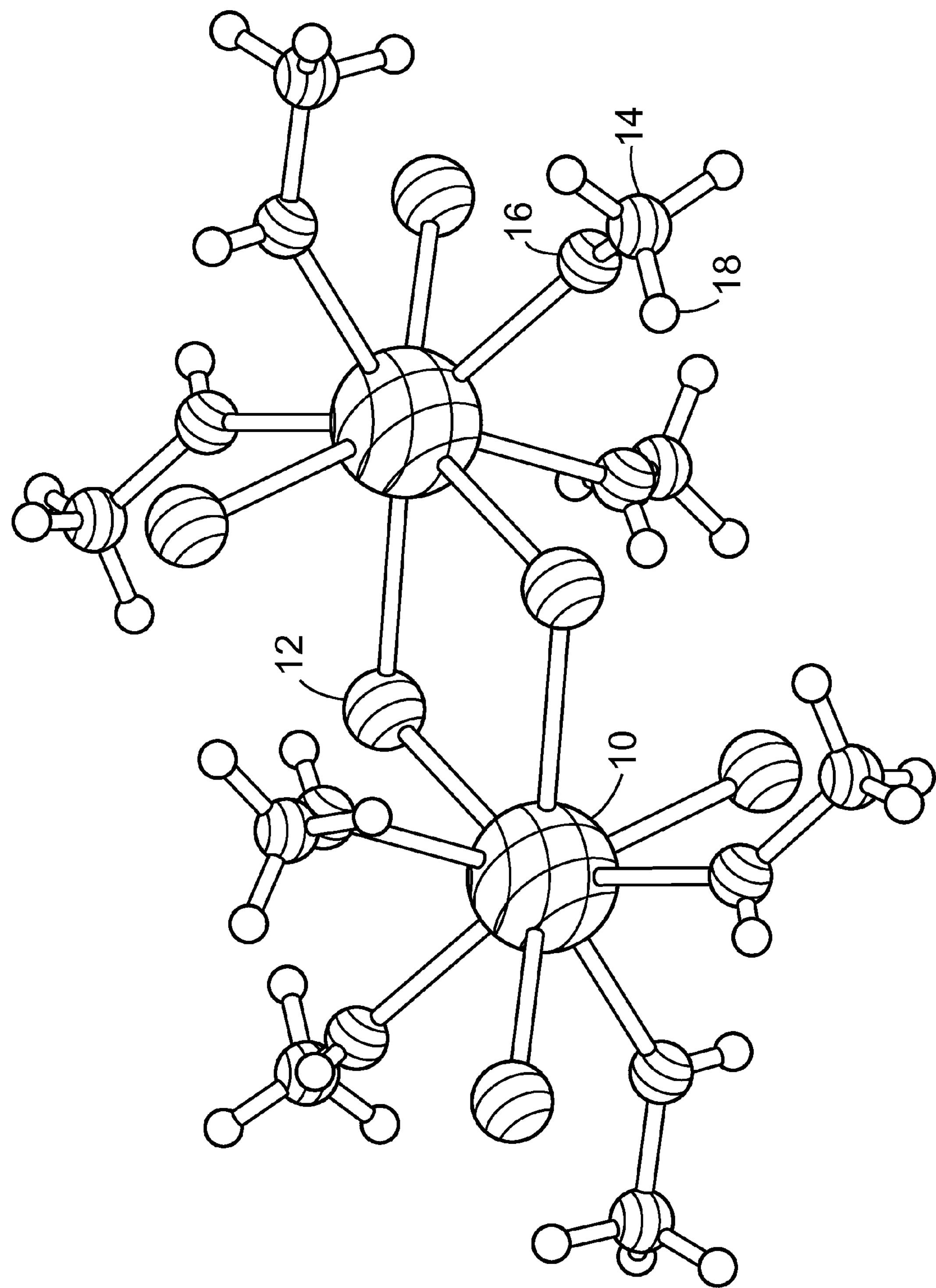
FIG. 1 is a perspective, schematic view of a $Ce_2Cl_6(CH_3OH)_8$ adduct molecular model in accordance with an example of the present invention.

The present invention provides a new scintillator crystal based on, for example, the metal-organic composition $CeCl_3(CH_3OH)_4$, which is a methanol adduct of cerium trichloride, $CeCl_3$. The crystal structure of $CeCl_3(CH_3OH)_4$, is shown in FIG. 1, having component atoms of elements cerium 10, chlorine 12, carbon 14, oxygen 16, and hydrogen 18 represented by respective patterned spheres.

The $CeCl_3(CH_3OH)_4$ crystal represents the first example of a rare-earth metal-organic scintillator that is applicable to X-ray, γ-ray, and neutron detection. A family of lanthanide trihalide methanol adduct compositions is contemplated in accordance with the present invention, expressed as a general formula $LX_3(CH_3OH)_4$ where L is an element selected from Y, Sc, and the lanthanide elements, and X is a halogen element. Examples of lanthanide elements include La, Ce, Pr, Nd, Pm, Sm, Eu, Gd, Tb, Dy, Ho, Er, Tm, Yb, and Lu. Examples of halogen elements include fluorine, chlorine, bromine, and iodine. All of the above described compositions are contemplated to have various scintillation properties that are useful for radiation detection applications.

Large single crystals of the above described compositions can be grown from a methanol solution at a temperature of about 65° C. or below. The high solubility of the compositions is consistent with the application of rapid solution growth methods similar to those methods conventionally applied to the commercial production of very large single crystals of potassium dihydrogen phosphate (KDP).

For example, $CeCl_3(CH_3OH)_4$ crystals can be grown by slow cooling a solution of $CH_3OH$ supersaturated with $CeCl_3$. The solution is heated to a temperature near 65° C. and allowed to cool to below 65° C. under carefully controlled crystal growth conditions. Crystal growth conditions can include, for example, the use of a crystallizer such as a Holden-type crystallizer. In such an example, a $CeCl_3$ seed is attached to the crystallizer platform and suspended in the solution. The solution is cooled at a rate in the range of about 0.1 to 10° C. per 10 hours while the seed crystal is rotated in alternate directions at a speed in the range of 1 to 100 RPM, with directional changes at an interval in the range of 1 second to 10 minutes, with a pause between directional changes in the range of 1 second to 5 minutes. This process is carried out until a crystal of the desired dimensions is grown. In about 24 hours, a crystal having dimensions of up to about 4×3.5×1.5 $cm^3$ can be grown, as shown and described in the following example.

EXAMPLE

Large, colorless crystals of $CeCl_3(CH_3OH)_4$ with dimensions up to 4×3.5×1.5 $cm^3$ were grown by slow cooling methanol solutions that were supersaturated and reacted with anhydrous $CeCl_3$. Apparatus used for the growth of $CeCl_3(CH_3OH)_4$ single crystals included a 4 L borosilicate glass growth vessel suspended in a 20 L thermal water bath container. The growth vessel was capped by a borosilicate glass lid with o-ring seal and secured with an aluminum ring clamp.

The solution was prepared by dissolving and reacting dry, purified cerium tri-chloride in anhydrous methanol. The solution was heated to approximately 65° C. and stirred by means of a magnetic stirring rod on a stirring hot plate. Approximately 540 g of $CeCl_3$ was initially dissolved in 1800 ml of methanol and allowed to stir for approximately one hr. The hot solution was then filtered through a glass micro-fiber filter to remove suspended particulate matter larger than 0.5 microns. The solution was then poured into the growth vessel and submerged in the water bath at 60° C. Due to evaporation and handling losses, the net volume of solution was approximately 1200 ml.

The solution was allowed to cool to approximately 50° C. at which point a platinum mesh basket with approximately 50 g of $CeCl_3$ was suspended in the solution and allowed to remain for approximately 24 hrs until signs of nucleation and crystallization were observed. This crystallization indicated that the solution had become supersaturated, and the basket was subsequently removed and the solution heated to 60° C. for 2 hrs to re-dissolve the solids.

The $CeCl_3$-methanol solution was allowed to cool to approximately 50° C. at which point a $CeCl_3$ crystal seed was attached to the growth platform in a Holden-type crystallizer with two small diameter platinum wires and positioned in the solution. The growth platform was placed in the solution such that the position of the seed crystal was located at the mid-point of the depth of the solution. The surrounding thermal water bath level was adjusted so that the level of solution within the growth vessel was approximately 2.5 cm higher than the level of the water bath to suppress spurious nucleation. The growth platform holding the seed crystal was rotated in alternate directions at a speed of approximately 60 rpm at 10-12 s intervals with a 2-4 s pause between directional changes. Two type K thermocouples were utilized, one for the control of a temperature controller/programmer, and the other connected to a digital temperature indicator to provide solution temperature readings. The thermal water bath temperature was controlled to allow for a 1° C. reduction in temperature per period of 10 hrs. Crystal growth was allowed to continue for a total growth time of 24 hrs at which time the crystals were removed from the vessel, rinsed clean of the solution in fresh anhydrous methanol, dried, and sealed under dry inert gas.

Crystals grown according to the above example were analyzed. X-ray single crystal structural refinement was carried out using Mo—Kα radiation (λ=0.71073 Å) a T=173K with a numerical absorption correction, μ(Mo—Kα)=4.24 $cm^{-1}$ and a transmission of 0.362-0.652. The data were collected using a Bruker SMART three-APEX CCD diffractometer. The pertinent data collection information is 16040 measured reflections, 3110 unique reflections ($R_{int}$=0.0183), 3053 observed reflections (I>2.00σ(I)), 130 parameters, R=0.014, wR=0.034, refined against $F^2$, and GOF=1.091. The SHELXTL Version 5 series of programs was used for the solution and refinement of the crystal structure. The hydrogen positions were fixed at ideal positions and the methyl group orientation was determined by a difference electron density synthesis.

Figure 2:
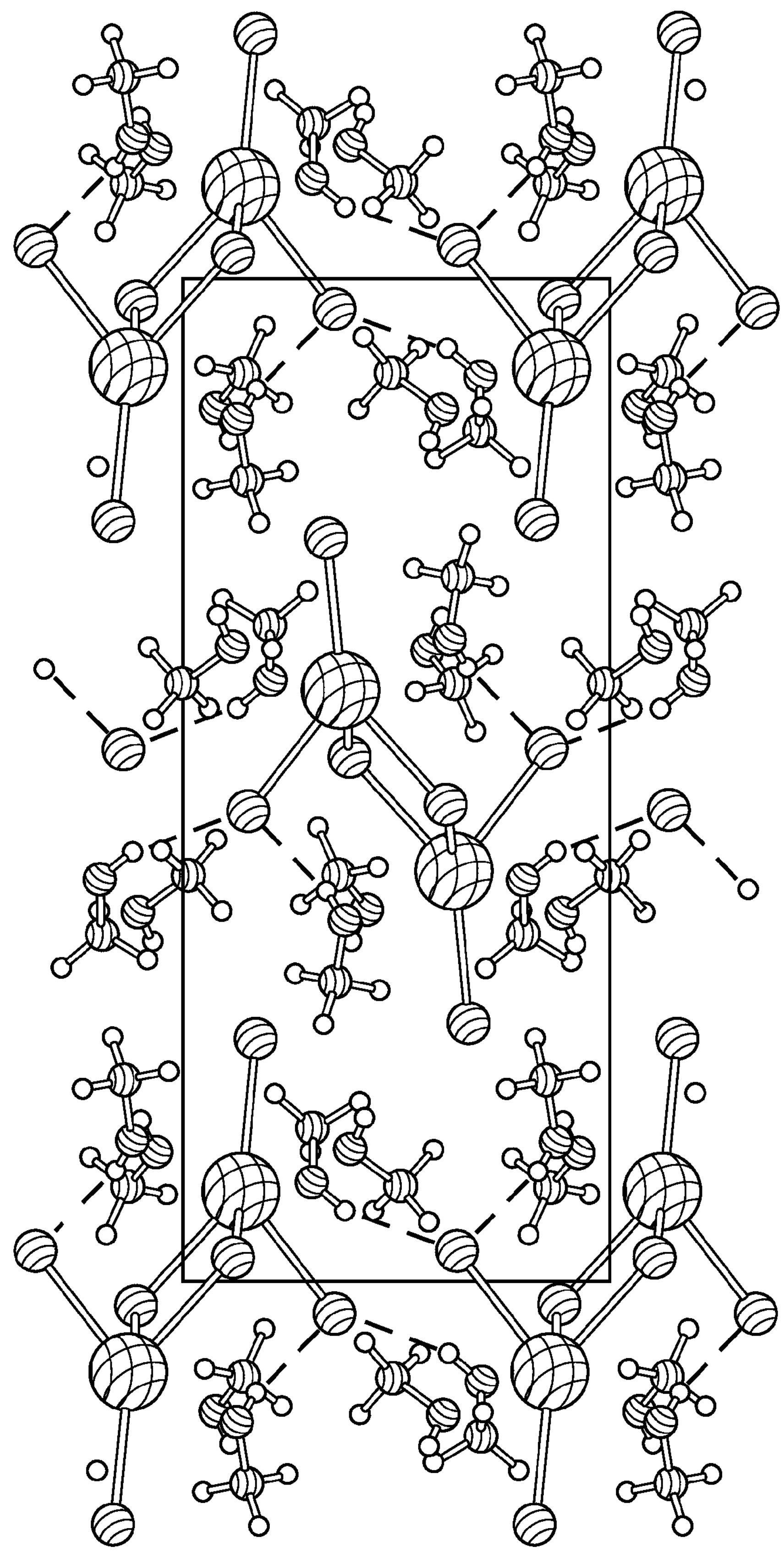
FIG. 2 is a perspective, schematic view of a cerium chloride-methanol adduct crystal molecular model, along the principal direction 100, in accordance with an example of the present invention.
Figure 3:
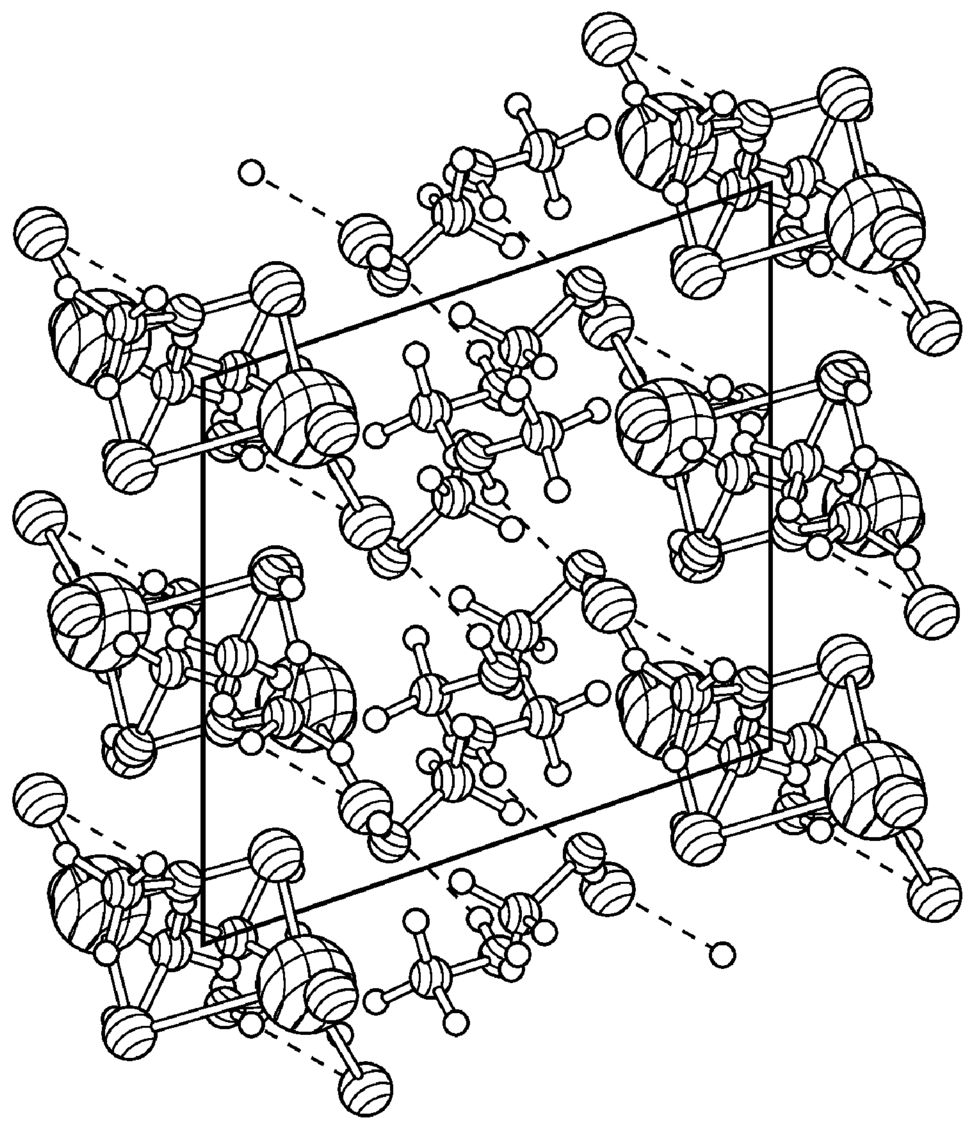
FIG. 3 is a perspective, schematic view of a cerium chloride-methanol adduct crystal molecular model, along the principal direction 010, in accordance with an example of the present invention.
Figure 4:
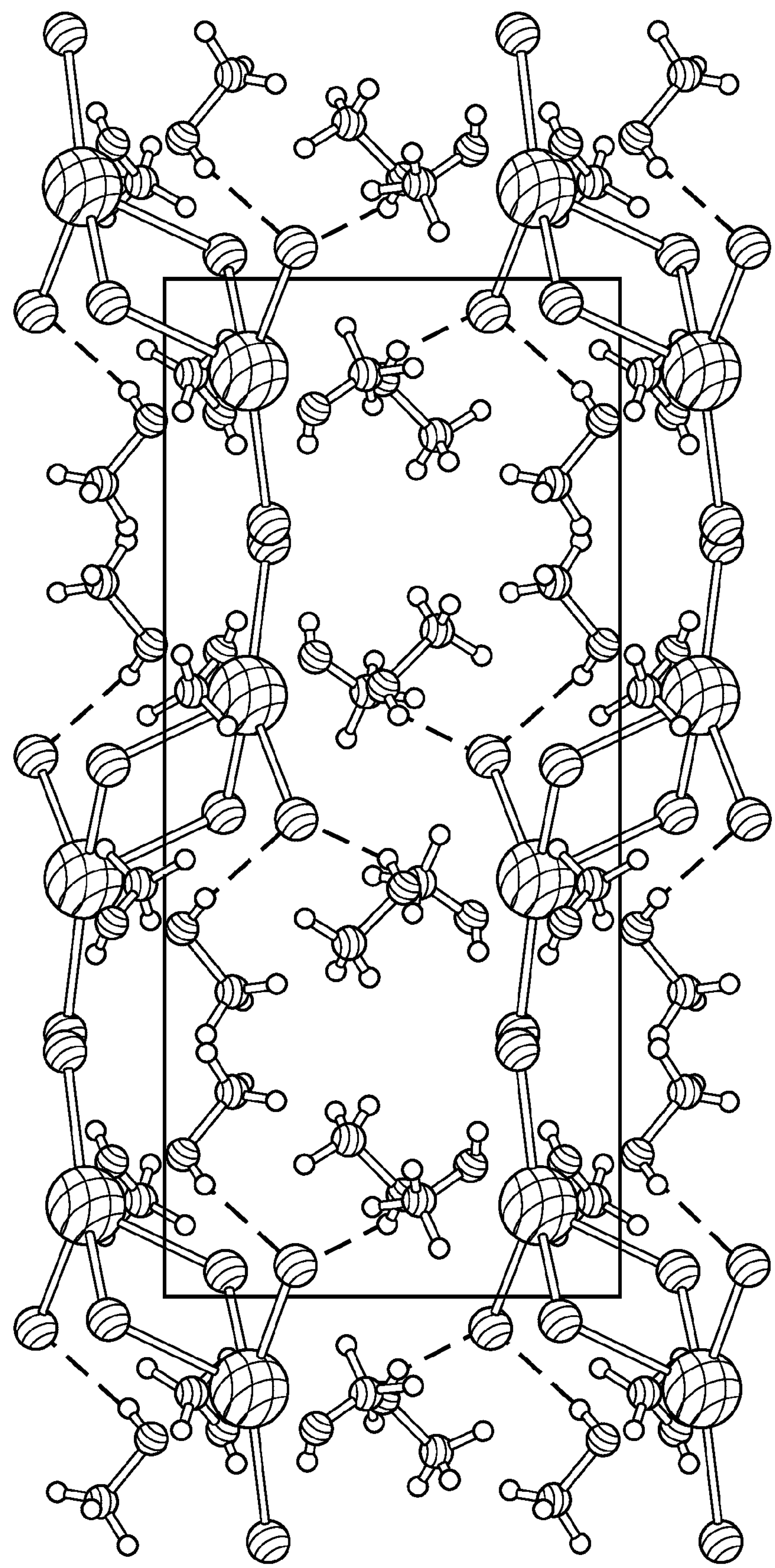
FIG. 4 is a perspective, schematic view of a cerium chloride-methanol adduct crystal molecular model, along the principal direction 001, in accordance with an example of the present invention.

The basic $C_4H_{16}CeCl_3O_4$ crystal data resulting from the single crystal X-ray structural refinement are: M=374.64, monoclinic structure, space group $P2_1/c$ (no. 14), a=8.7092 (5), b=18.5100(9), c=8.2392(4) Å, β=108.946(1)°, V=1256.2 (1) $Å^3$, Z=4, and $D_{calc}$=1.981 g/$cm^3$. The $CeCl_3$-methanol adduct has a center of symmetry only, although the molecular packing gives the crystal monoclinic symmetry overall. The Ce coordination is eightfold, and is a square anti-prism. The Ce—Cl bond lengths involved in the edge-sharing dimer, 2.8517(4), 2.9233(4) Å and their ratio 0.975, are quite similar to those reported for $Ce_2Cl_6(DME)_4$, 2.884(1), 2.927(1) Å, and 0.985[3]. The bond valence sums to the Ce are consistent with the expected trivalent state. The C—O bond lengths in the methanol adduct are only slightly longer (having a mean of 1.433(5) Å) than that observed in methanol, 1.41(1) Å, with the differences associated with their bonded interaction with Ce. The methanol takes part in intermolecular hydrogen bonding to the terminal Cl atoms in neighboring molecules as seen in FIGS. 2-4. The atomic displacements of the methyl groups are not overly large, which reflects the property that their libration and rotation are constrained by the hydrogen-bonding network. The hydrogen-bond network illustrated in FIGS. 2-4 creates a 3-dimensional framework, but the crystals cleave easily along the 100 plane.

Figure 5:
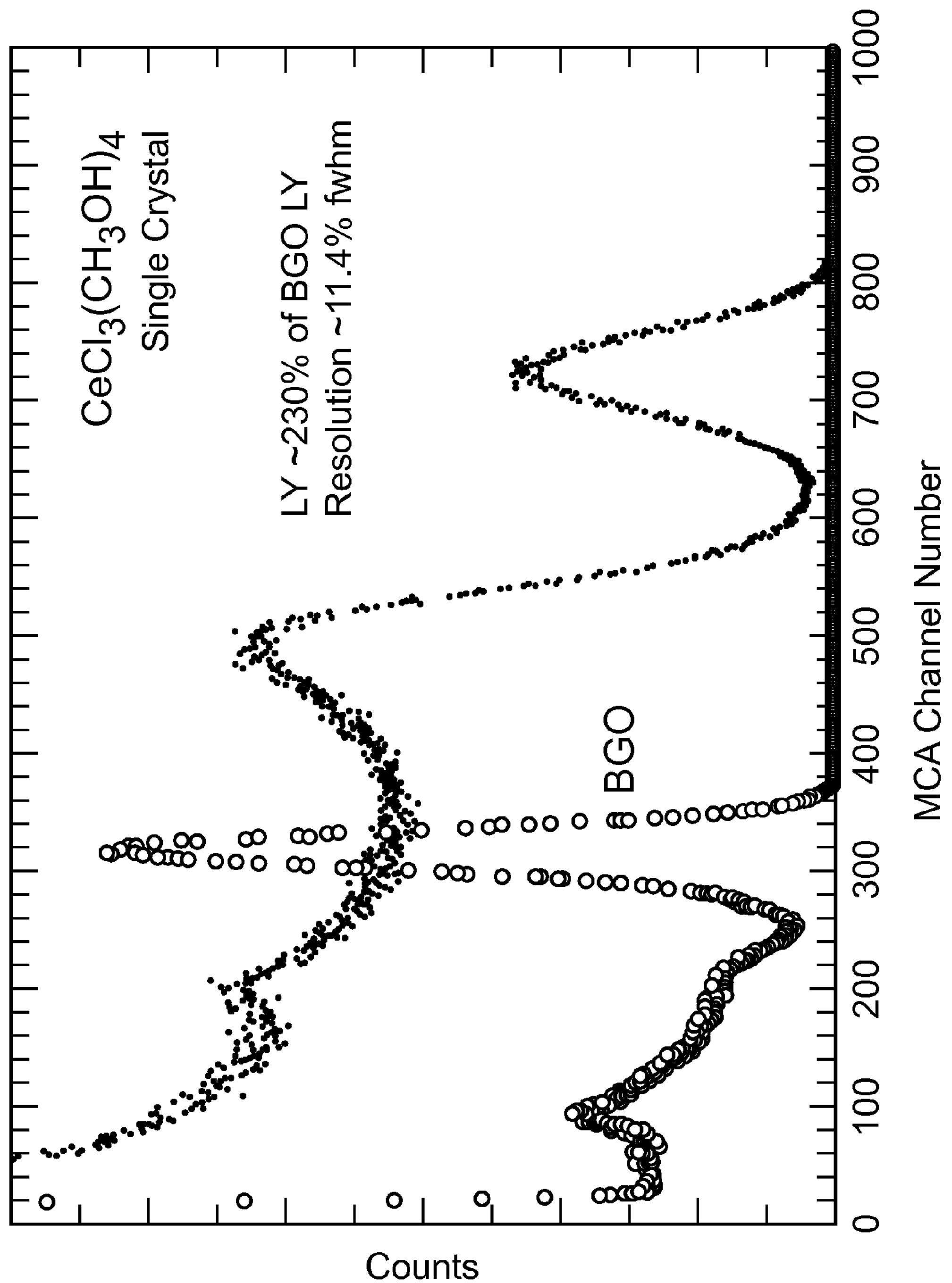
FIG. 5 is a graph showing the Energy spectrum of a $CeCl_3(CH_3OH)_4$ metal-organic scintillator single crystal obtained using 662 keV γ-rays (gamma rays) from a $^{137}Cs$ 1 micro curie source.
Figure 6:
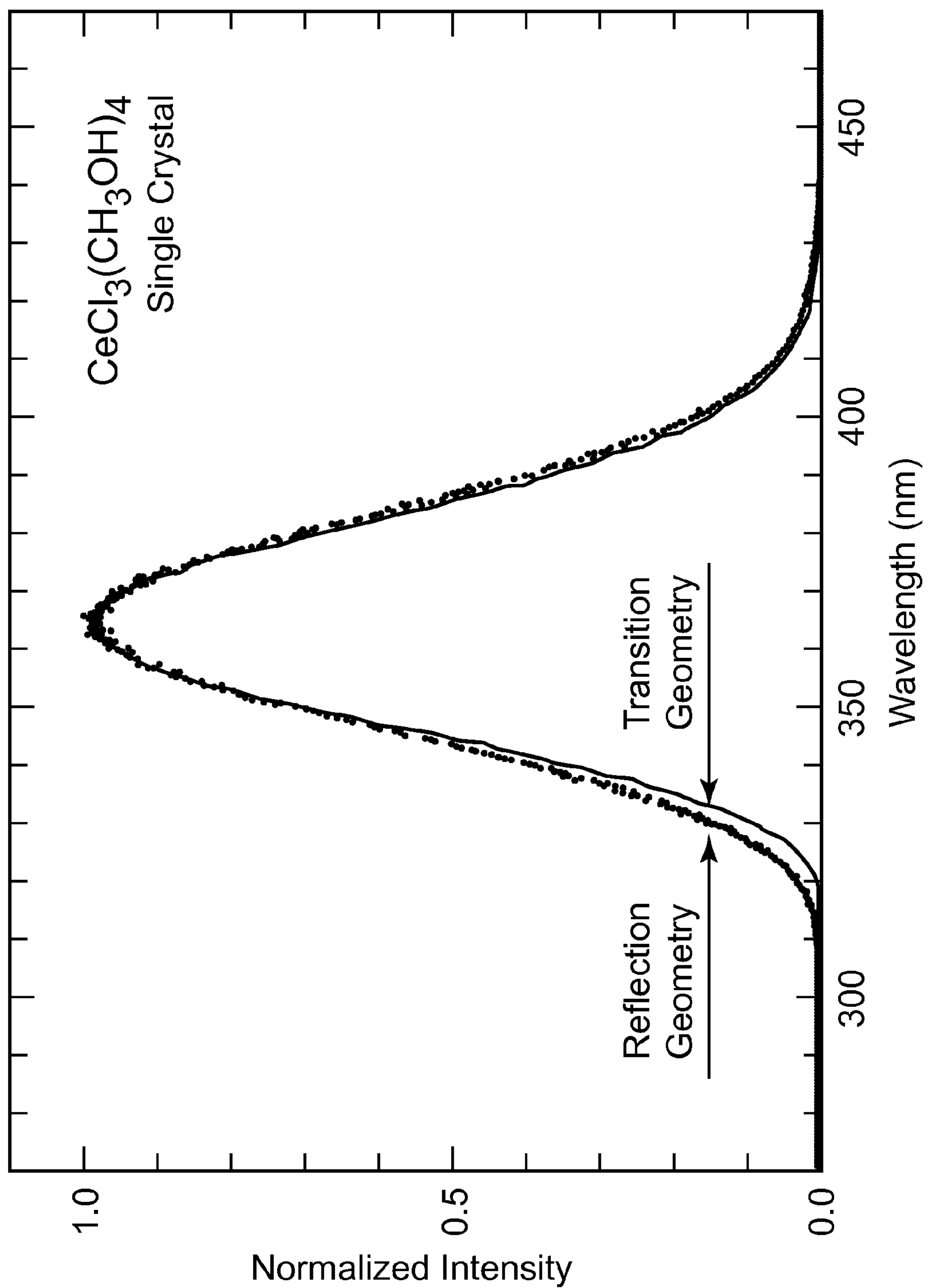
FIG. 6 is a graph showing X-ray-excited luminescence spectrum for a single crystal of $CeCl_3(CH_3OH)_4$ measured in both transmission and reflection geometries using excitation at 35 kV.

$CeCl_3(CH_3OH)_4$ represents, to our knowledge, the first example of a rare-earth metal-organic scintillator for use in γ-ray, X-ray, and fast neutron detection. Measurements were made using both Cf-252 spontaneous fission neutrons and 14.1 MeV neutrons from a D-T generator. Energy spectra of the cerium chloride-methanol adduct single crystals, shown in FIG. 5, were obtained using 662 keV γ-ray photons from a 1 μCi source. Using a shaping time of 0.5 μs, plus 4 layers of Teflon tape covering the top of the sample and optical coupling fluid between the sample and the photomultiplier tube for light collection purposes, light yields of ~16,600 photons/MeV were obtained by comparison with the light yield from a 1×1×1 $cm^3$ bismuth germanium oxide (BGO) reference scintillator crystal. The $CeCl_3(CH_3OH)_4$ light yield was 260% of that of a BGO scintillator with a light yield of 6400 photons/MeV yielding a value of 16,600 photons/MeV for $CeCl_3(CH_3OH)_4$ without corrections for the photomultiplier tube efficiency. Using the same experimental configuration described above, an energy resolution of 11.2% was obtained at 662 keV. The $CeCl_3(CH_3OH)_4$ scintillator decay time for γ-ray excitation was measured using the time-correlated single-photon-counting (Bollinger-Thomas) method, and a nominal value of 59 nsec was obtained. X-ray-excited luminescence spectra shown in FIG. 6 were measured at an excitation energy of 35 kV in both reflection and transmission geometries. The peak emission of the X-ray excited luminescence spectrum occurs at 370 nm.

While there has been shown and described what are at present considered to be examples of the invention, it will be obvious to those skilled in the art that various changes and modifications can be prepared therein without departing from the scope of the inventions defined by the appended claims.

What is claimed is:

1. A metal-organic composition comprising a lanthanide trihalide methanol adduct having the chemical formula $CeX_3(CH_3OH)_4$ wherein X is a halogen element.

2. A metal-organic composition in accordance with claim 1 wherein said chemical formula is $CeCl_3(CH_3OH)_4$.

3. A metal-organic scintillator comprising a crystal having the chemical formula $CeX_3(CH_3OH)_4$ wherein X is a halogen element.

4. A metal-organic scintillator in accordance with claim 3 wherein said chemical formula is $CeCl_3(CH_3OH)_4$.

5. A radiation detector comprising a metal-organic scintillator comprising a. a crystal having the chemical formula $CeX_3(CH_3OH)_4$ wherein X is a halogen element; and b. a photodetector being coupled to said crystal, so that upon exposure of said inorganic scintillating material to radiation said inorganic scintillating material emits light.

6. A radiation detector in accordance with claim 5 wherein said chemical formula is $CeCl_3(CH_3OH)_4$.

7. A radiation detector in accordance with claim 5 wherein said radiation comprises at least one form of radiation selected from the group consisting of x-ray radiation, γ-radiation, and fast neutron radiation.

8. A method of detecting radiation comprising the steps of:

a. receiving radiation with a metal-organic scintillator comprising a crystal having the chemical formula $CeX_3(CH_3OH)_4$ wherein X is a halogen element;

b. emitting light with said crystal in response to said step of receiving said radiation; and c. detecting said light with a photodetector.

9. A method of detecting radiation in accordance with claim 8 wherein said chemical formula is $CeCl_3(CH_3OH)_4$.

10. A method of detecting radiation in accordance with claim 8 wherein said radiation comprises at least one form of radiation selected from the group consisting of x-ray radiation, γ-radiation, and fast neutron radiation.

* * * * *